United States Patent [19]
Lara

[11] Patent Number: 5,233,297
[45] Date of Patent: Aug. 3, 1993

[54] TRANSIENT ELECTROMAGNETIC METHOD AND APPARATUS FOR INSPECTING CONDUCTIVE OBJECTS UTILIZING SENSORS THAT MOVE DURING INSPECTION

[75] Inventor: Pedro F. Lara, Dallas, Tex.

[73] Assignee: Atlantic Richfield Company, Los Angeles, Calif.

[21] Appl. No.: 563,055

[22] Filed: Aug. 6, 1990

[51] Int. Cl.$^5$ .............. G01N 27/72; G01N 27/82; G01R 33/12; G01B 7/10
[52] U.S. Cl. .................. 324/220; 324/229; 324/240
[58] Field of Search ........... 324/219, 220, 221, 229, 324/230, 231, 238, 239, 240, 241, 242, 243

[56] References Cited

U.S. PATENT DOCUMENTS

| | | | |
|---|---|---|---|
| 2,965,840 | 12/1960 | Renken, Jr. et al. | 324/240 |
| 3,090,910 | 5/1963 | Moran | 324/221 |
| 3,189,817 | 6/1965 | Renken, Jr. | 324/240 |
| 3,229,197 | 1/1966 | Renken, Jr. | 324/240 |
| 3,532,969 | 10/1970 | McCullough et al. | 324/34 |
| 3,745,452 | 7/1973 | Osburn et al. | 324/54 |
| 3,852,659 | 12/1974 | Barringer | 324/6 |
| 4,188,577 | 2/1980 | Mhatre et al. | 324/220 |
| 4,445,088 | 4/1984 | Schübel | 324/238 |
| 4,839,593 | 6/1989 | Spies | 324/240 |
| 4,843,319 | 6/1989 | Lara | 324/240 |
| 4,843,320 | 6/1989 | Spies | 324/240 |
| 4,954,778 | 9/1990 | Champonnios et al. | 324/240 |

Primary Examiner—Walter E. Snow
Attorney, Agent, or Firm—Geoffrey A. Mantooth

[57] ABSTRACT

There is provided a transient electromagnetic method and apparatus for inspecting objects using moving sensors. The apparatus includes a sensing portion, which has a transmitting antenna and at least one receiving antenna thereon. The sensing portion is located adjacent to the object which is to be inspected such that the antennas are adjacent to the object. The sensing portion is moved along the object at the same time the transmitting antenna is inducing current in the wall and the receiving antenna is producing a received signal of the induced current diffusion in the wall. Because the antennas are moving during data acquisition, the speed of inspection is increased. The data is then interpreted to determine the thickness of the object.

10 Claims, 11 Drawing Sheets

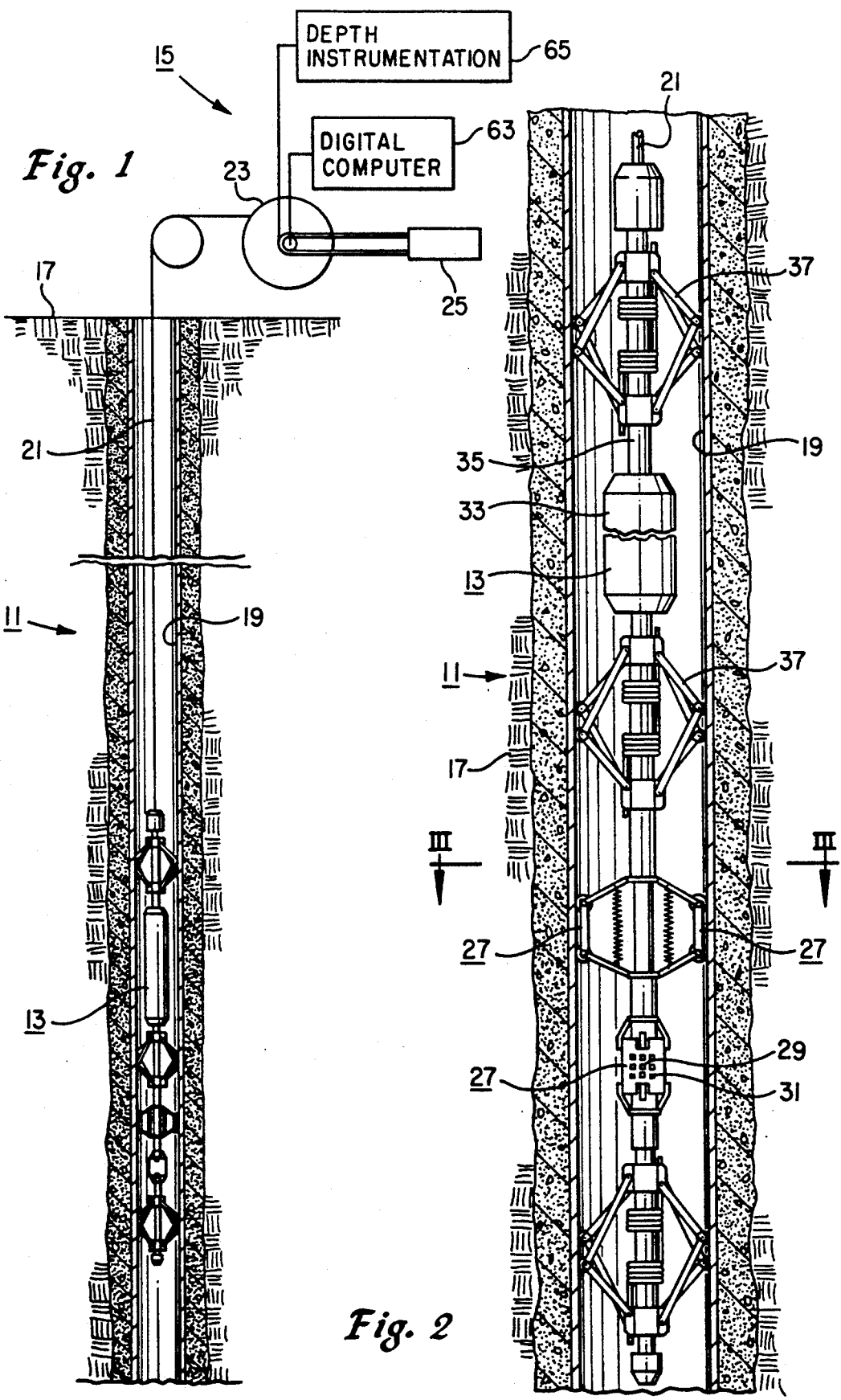

TRANSIENT ELECTROMAGNETIC METHOD AND APPARATUS FOR INSPECTING CONDUCTIVE OBJECTS UTILIZING SENSORS THAT MOVE DURING INSPECTION

FIELD OF THE INVENTION

The present invention relates to methods and apparatuses for non-destructively inspecting objects, such as pipelines, storage tanks, etc., for corrosion and the like.

BACKGROUND OF THE INVENTION

The use of transient electromagnetic techniques to inspect containers such as pipelines is disclosed in Spies U.S. Pat. No. 4,843,320 and in Lara U.S. Pat. No. 4,843,319, which patents are owned by the assignee of the present invention. The '320 patent is directed to a transient electromagnetic method for detecting corrosion on conductive objects. Often, such objects are wrapped in insulation to either prevent undue heat loss or to protect personnel from hazards. The transient electromagnetic method of the '320 patent can penetrate the insulation to probe the conductive wall underneath. This layer of insulation may vary in thickness from one location to another along the container wall. My '319 patent provides a method for compensating for variations in the thickness of insulation.

The transient electromagnetic method of the '320 and '319 patents requires placing a transmitting antenna and a receiving antenna in proximity to the object. In the case of an insulated pipeline, the antennas are placed on top of the insulation. The transmitting antenna then induces a current into the pipeline wall, which current decays rapidly. The decay of the induced current is detected by the receiving antenna. By analyzing the induced current decay, a measurement of wall thickness can be obtained. Corrosion acts to reduce wall thickness, thus any reduction in wall thickness can be determined from the TEM measurement.

As shown in the '320 and '319 patents, the transient electromagnetic method is unconcerned with the speed of data acquisition. However, there exists many situations where speed of the inspection process is of primary concern. This is particularly true in downhole tubing, heat exchanger tubing and buried fluid transmission pipelines where, because of the situs of the tubing or pipeline, the antennas must be located interiorly of the tubing or pipeline. As a result of using interiorly located antennas, downtime is incurred. Lengthy downtimes produced by the use of stationary antennas are costly and are therefore avoided in practice.

Prior art technologies are not very satisfactory for inspecting downhole tubing and the like. Ultrasonic methods have narrow resolutions that add to inspection time. Also, the ultrasonic transducers are affected by fluid coupling from the fluid inside of the tubing or pipeline. Flux leakage methods have no such coupling problem, but there is a problem with interpreting the data. The signals are strongly affected by sharp edges, and make interpretation difficult.

Transient electromagnetic methods do not suffer these disadvantages. Therefore, it is desirable to increase the speed of transient electromagnetic inspections of an object. With such an inspection system, larger areas could be inspected within shorter periods of time. Furthermore, with such an inspection system, the antennas could be placed inside of pipelines and not impede the flow of fluid. Thus, the pipelines undergoing inspection could remain in use.

SUMMARY OF THE INVENTION

It is an object of the present invention to provide a transient electromagnetic method and apparatus for inspecting objects, wherein the sensors that are used for inspecting are able to move along the object during the inspection.

The apparatus of the present invention includes a sensing portion that is adapted to be located in proximity to a conductive object. The sensing portion includes transmitting antenna means and receiving antenna means. Transmitter means is connected with the transmitting antenna means. The transmitter means produces an abruptly changing current in the transmitting antenna means. Receiver means is connected with the receiving antenna means. A controller means for controlling the operation of the transmitter means and the receiver means is provided. The transmitter means operates intermittently and the receiver means detects induced currents in the object after each operation of the transmitter means. There is also provided means for automatically moving the sensing portion along the object during the operation of the transmitter means and the receiver means.

In one aspect, the moving means includes a motor and a drum. The sensing portion is connected to the drum by a cable, wherein the sensing portion is moved along the object by rotating the drum.

In another aspect, the sensing portion includes plural receiving antenna means. A first receiving antenna means is located laterally of the transmitting antenna means such that a first imaginary line extending from the transmitting antenna means to the receiving antenna means is perpendicular to the direction of motion of the sensing portion. A second receiving antenna means is located relative to the transmitting antenna means such that a second imaginary line extending from the transmitting antenna means to the second receiving antenna means is parallel to the direction of motion of the sensing portion. A third receiving antenna means is provided, which is coincident to the transmitting antenna means.

The method of inspecting a conductive object includes the steps of providing transmitting antenna means and transmitter means connected with the transmitting antenna means, and providing receiving antenna means and receiver means connected with the receiving antenna means. The transmitting antenna means and the receiving antenna means are located in proximity to the object. The transmitting antenna means and the receiving antenna means are moved along the object. While moving the transmitting antennas and the receiving antenna means along the object, providing an abruptly changing current to the transmitting antenna means from the transmitter means so as to induce current into the object and then detecting the induced current in the object with the receiving antenna means to produce the received signal. The thickness of the object is determined from the received signal by determining with respect to time the derivative of the received signal and comparing that derivative to a derivative of a reference signal. The reference signal is obtained from a reference object of known thickness. As the transmitting antenna means and the receiving antenna means are moved along the object current is induced into the object and received so as to produce received signals. These received signals are then processed to determine the thickness of the object.

With the present invention, a conductive object such as a wall and a pipeline, heat exchanger tubing or casing can be inspected for wall loss due to corrosion. The speed of inspection is increased with the present invention because data acquisition can occur while the antennas are moving along the wall.

BRIEF DESCRIPTION OF THE DRAWINGS

FIG. 1 is a cross-sectional side view of a borehole and surface equipment, showing the apparatus of the present invention, in accordance with a preferred embodiment.

FIG. 2 is a close-up view of the downhole apparatus of FIG. 1.

FIG. 8 is a cross-sectional view of a length of heat exchanger tubing, showing the apparatus of the present invention, in accordance with a preferred embodiment.

DESCRIPTION OF PREFERRED EMBODIMENTS

Figure 3:
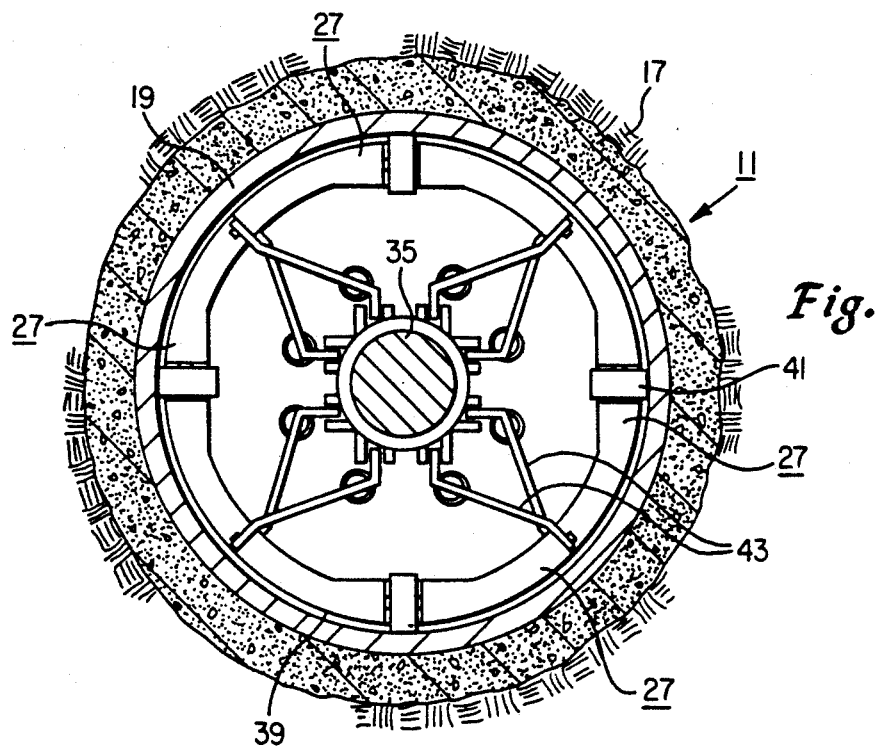
FIG. 3 is a transverse cross-sectional view of the apparatus, taken along lines III—III of FIG. 2.

Generally speaking, to probe a conductive wall using transient electromagnetic techniques, electromagnetic transmitting and receiving sensors are required. The transmitting and receiving sensors are located adjacent to the wall and the transmitting sensor is provided with an abruptly changing current. The transmitting sensor induces a current into the wall, which induced current is detected by the receiving sensor. A received signal is produced by the receiving sensor that represents the induced current. This received signal is then analyzed to determine the thickness of the wall at the sensor location. By knowing the original thickness of the wall, a reduction in thickness can be discovered. If it is found that the wall thickness has been reduced, then the presence of corrosion or some other thickness reducing mechanism can be deduced.

Prior art TEM methods of probing conductive walls have utilized stationary transmitting and receiving antennas. Stationary antennas are utilized in order to acquire plural received signals for each antenna location. The plural signals are then stacked to increase the signal-to-noise ratio. The prior art is shown in U.S. Pat. Nos. 4,843,320 and 4,843,319. The disclosures of the '320 and '319 patents are incorporated by reference herein.

I have discovered that the transmitting and receiving antennas can be moved along the wall while the antennas are engaged in data acquisition by inducing currents into the wall and detecting the induced currents. I have found that moving the transmitting and receiving antennas over the wall not only speeds data acquisition, but produces data that can be interpreted for wall thickness. Methods that use moving transmitting and receiving antennas are particularly useful in determining the wall thickness of downhole tubing, heat exchanger tubing and pipelines.

In FIGS. 1 and 2, there is shown a schematic longitudinal cross-sectional view of a cased well borehole 11, showing an electromagnetic logging apparatus 13 located therein, and supporting surface equipment 15, with which the method of the present invention, in accordance with a preferred embodiment, can be practiced.

The well borehole 11, which is drilled into the earth 17, is an oil or gas well. The well borehole 11 is lined with a length of casing 19 that is cemented in place in the borehole. The casing 19 is made of a conductive material such as steel.

The logging apparatus 13 is located within the casing 19 and moves up and down the borehole for logging operations. The logging apparatus 13 is suspended inside of the casing 19 by a logging cable 21, which provides electrical power and data communications channels from the surface equipment 15. On the surface, the logging cable is wound around a drum 23. A motor 25 rotates the drum to lower and raise the logging apparatus 13 inside of the borehole 11.

Referring to FIG. 2, the logging apparatus 13 includes plural sensing heads 27 that contain the transmitting and receiving antennas 29, 31, downhole electronics 33, and a body member 35. The body member 35 is cylindrical and elongated. Centralizers 37 are positioned along the body member 35 to maintain the logging apparatus in a centered position along the longitudinal axis of the casing 19.

There are provided four sensing heads 27 in the preferred embodiment (see FIGS. 2 and 3). The sensing heads 27 are disposed 90 degrees apart around the circumference of the body member 35 and are large enough to provide 360 degrees circumferential coverage of the casing. To prevent contact between adjacent sensing heads, the sensing heads 27 are longitudinally displaced from each other along the body member. Thus, there is an upper pair of sensing heads and a lower pair of sensing heads. Each pair has two diametrically opposed sensing heads. The lower pair is rotated 90 degrees from the upper pair to provide for complete circumferential coverage. Each sensing head has an arcuately shaped outer surface 39 that approximately corresponds to the curvature of the inside surface of the casing 19. Each sensing head 27 has a pair of rollers 41 thereon for contact with the casing 19 (see FIG. 4). The rollers 41 protrude out slightly from the outer surface 39 of each sensing head, so that the antennas 29, 31 are protected from abrasion with the casing wall 19. Each sensing head 27 is mounted onto the body member 35 by a pair of arms 43. The arms 43, which are spring loaded, force the sensing head into rolling contact with the inside surface of the casing.

Figure 4:
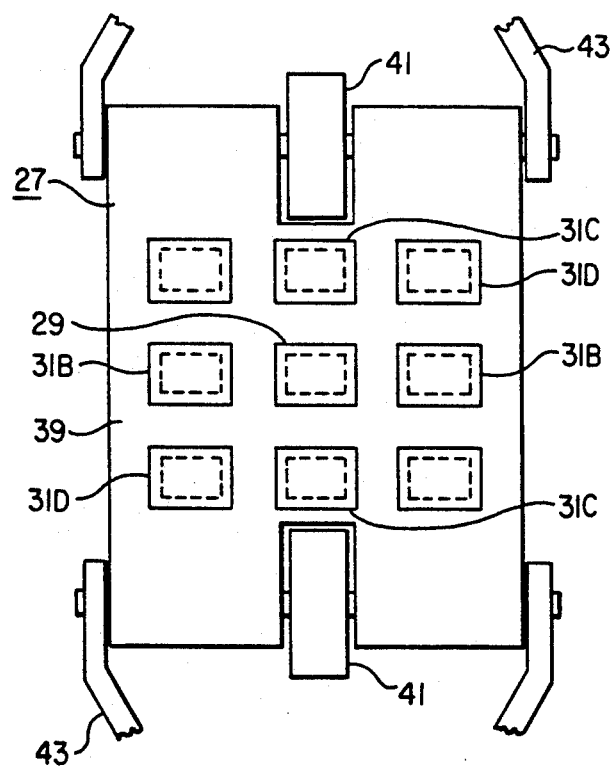
FIG. 4 is a front side view of a sensor head assembly.
Figure 5:
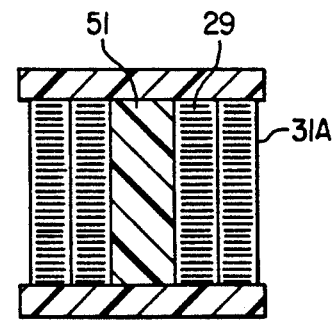
FIG. 5 is a cross-sectional view of the transmitting and receiving coil arrangement.
Figure 6:
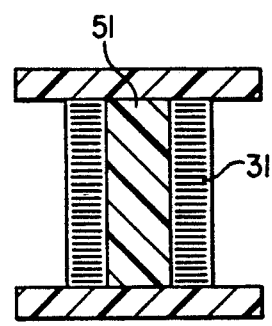
FIG. 6 is a cross-sectional view of the receiving coil arrangement.

Each sensing head 27 (see FIG. 4) has plural antennas located thereon so as to be adjacent to the casing wall. In the center of each sensing head 27 is a transmitting antenna 27 and a coincident receiving antenna 31A. Both transmitting and receiving antennas 29, 31A are wound onto the same core 51, as shown in FIG. 5. The core 51, which is in the shape of a spool, is made of a non-magnetic and non-conductive material such as plastic. The respective antennas are made up of respective coils of wire. There are also provided plural receiving antennas located around the central transmitting antenna 29. Each receiving antenna 31 is made up of a coil of wire wrapped onto a core 51 (see FIG. 6). The antennas are oriented in the sensing head 27 so that the longitudinal axes of the cores 51 are perpendicular to the adjacent portion of casing walls.

The receiving antennas 31 other than the coincident antenna 31A are placed in various spatial orientations with respect to the transmitting antenna 29. Thus, there are receiving antennas 31B that are located laterally or transversely from the transmitting antenna 29. The transverse antennas 31B are located along a first imaginary line extending between the respective transverse antenna and the transmitting antenna 29, which first imaginary line is perpendicular to the direction o motion of the transmitting antenna. There are also receiving antennas 31C that are located longitudinally from the transmitting antenna 29. The longitudinal antennas 31C are located along a second imaginary line extending between the respective longitudinal antenna and the transmitting antenna 29, which second imaginary line is parallel to the direction of motion of the transmitting antenna. And there are receiving antennas 31D that are located both transversely and longitudinally (diagonally) from the transmitting antenna 29.

Figure 7:
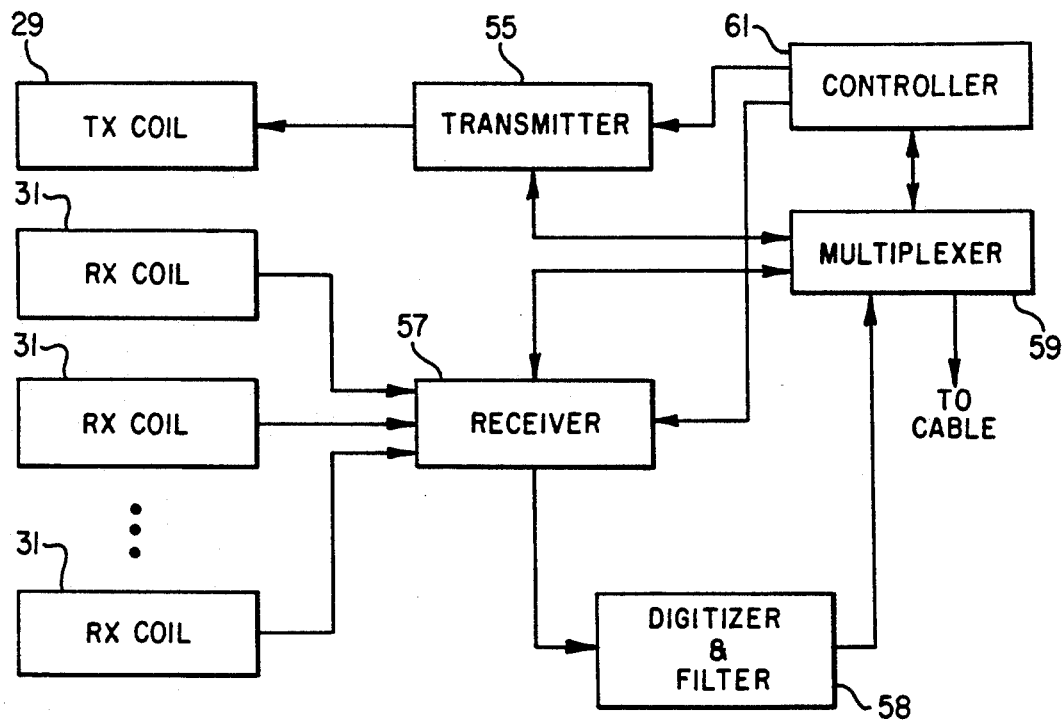

In FIG. 7, there is shown the transmitting and receiving antennas, that are contained in a sensing head, as connected to the downhole electronics. The transmitting antenna 29 in each sensing head 27 is connected to a transmitter 55. The transmitter 55 generates a pulse having abrupt fall times on the order of 1-100 microseconds. Typically, the pulse has amplitudes of one to two amps. The pulses of the transmitter pulse train alternate polarity to eliminate dc bias in the instrumentation. Thus, the first pulse is positive, the second pulse is negative, the third pulse is positive, the fourth pulse is negative and so on. The duration of each pulse is sufficiently long to stabilize the pulse magnitude so that there are no currents induced into the casing wall before the occurrence of the abrupt fall time of the pulse.

The respective receiving antennas 31 of each sensing head 27 are connected to a receiver 57. The receiver 57 is a multi-channel instrument, having a channel for each receiving antenna. The receiver 57 is a broad band instrument with a wide (5 or 6 order of magnitude) dynamic range. An analog-to-digital converter 58 digitizes the data from each receiving antenna. The digitized data is filtered for 60 Hz noise rejection and sent to a multiplexer 59 for transmission up the logging cable 21.

The downhole electronics may contain as many transmitters and receivers as required. In the preferred embodiment, there are four transmitting antennas 29, one for each sensing head 27. One transmitter may energize all four transmitting antennas; either simultaneously or sequentially, or plural transmitters may be used. Likewise, plural receivers may be used, to provide an appropriate number of receiver channels. An appropriate number of digitizers is also provided. A controller 61 is connected to the transmitter 55 and the receiver 57. The controller 61 coordinates data acquisition by the sensing heads by controlling the transmitter 55 and the receiver 57.

The surface equipment includes the drum 23 and the motor 25 (which are described above), a digital computer 63 and depth instrumentation 65 (see FIG. 1). On the surface, the data is received from the logging cable by the computer. The computer 63 is a conventional portable computer with sufficient memory capacity to record the data. The computer stores the data from the receiving antennas and performs some processing of the data. The depth instrumentation 65 tracks the depth of the logging apparatus in the hole.

The method of inspecting the wall of the downhole casing will now be described. The logging apparatus 13 is lowered down into the well 11 to the lowest point of inspection. Then, the logging apparatus 13 is raised toward the surface at a constant speed. With the logging apparatus located inside of the well casing, the rollers 41 of the sensing heads 27 contact the inside surface of the casing wall 19. The sensing heads 27 are forced into rolling contact with the casing wall by the arms 43 such that there is a gap between the transmitting and receiving antennas and the casing wall. The transmitting and receiving antennas on the sensing head are maintained at a relatively constant distance from the casing wall 19.

With the logging apparatus 13 being raised uphole, the transmitting antenna 29 on each sensing head 27 is energized by the transmitter 55. Each transmitting antenna 29 is energized for a sufficient length of time to stabilize the current in the antenna, thereby insuring no currents are induced into the casing wall. Then, each transmitting antenna 29 is abruptly deenergized by the transmitter, so that the current in the transmitting antenna rapidly falls to zero magnitude. This abrupt deenergization of the transmitting antenna induces current into that portion of the casing wall 19 that is adjacent to the respective transmitting antenna. As soon as the respective transmitting antenna is deenergized, the receiver 57 that is associated with the adjacent receiving antennas 31 is switched on. The respective receiving antennas 31 detect the presence of and the decay of the induced current in the casing wall and produce a respective received signal representing the induced current. The received signals are received by the receiver 57, where they are amplified and filtered, and then digitized by the digitizer 58. The received signals are then transmitted uphole over the logging cable by the multiplexer 59. At the surface, the computer 63 stores the received signals. The computer 63 processes the received signals to obtain a measurement of wall thickness.

Because the logging apparatus 13 is constantly moving, data is acquired during movement of the transmitting and receiving antennas 29, 31 along the casing wall 19. The transmitting and receiving antennas are located close to the casing wall (about ⅛ of an inch in the preferred embodiment) so as to produce a received signal having a high signal-to-noise ratio. This eliminates the need for acquiring plural received signals for stacking purposes for any given area of casing wall. Because only a single received signal is required for any given area of casing wall, the transmitting and receiving antennas need not be stationary, but can move along the casing wall during data acquisition. Thus, the transmitting antennas are abruptly deenergized when the sensing heads are at a first position relative to the casing wall. The abrupt deenergization induces current into the wall, which current diffuses away from the transmitting antenna. Data acquisition by the receiver 57 commences when the transmitting antenna is deenergized, and terminates a short time later, when the sensing heads are at a second position relative to the casing wall.

The speed of movement of the transmitting and receiving antennas with respect to the casing wall depends on the diffusion speed of the induced currents within the wall. The induced currents diffuse from the near surface of the wall (near the transmitting antenna) to the far surface of the wall and also diffuse radially outward much like the ripples caused by a pebble dropped into a body of water. The diffusion speed of the induced currents in the wall is a function of the wall material, wall thickness and geometry. For ease in interpreting the data, the antenna speed should be an order of magnitude less than the induced current diffusion speed. This would effectively render the antenna stationary with respect to the induced currents. For a pipe having an inside diameter of two inches and a nominal wall thickness of 0.185 inches, antenna speeds of 50 feet of pipe per minute or less would be less than the diffusion speed of the induced currents. The length of time for receiving the signals (and moving the sensing head between the first and second positions) is typically about 3-5 milliseconds.

Figure 9:
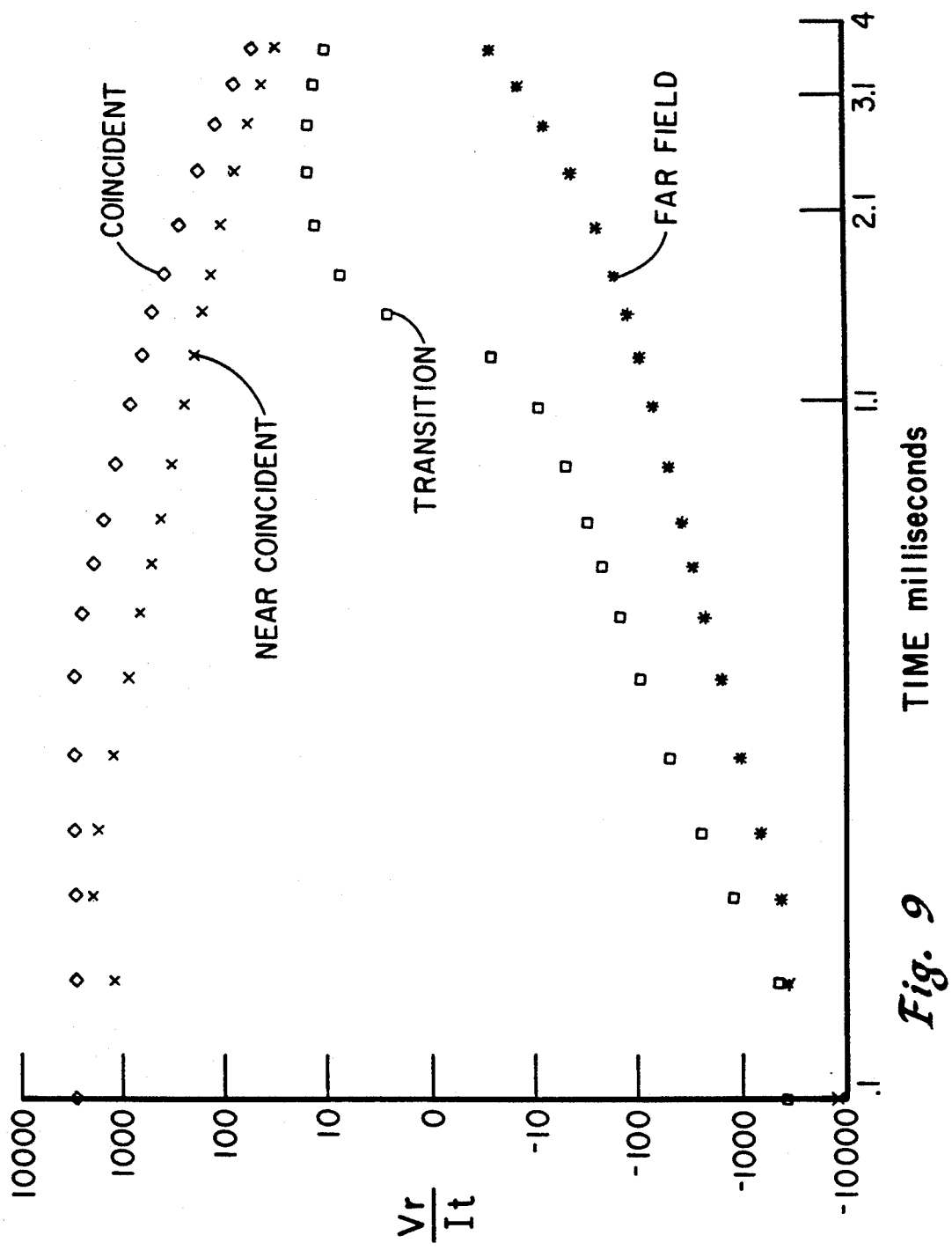
FIG. 9 is a graph showing plural decays of induced currents in a pipe wall, obtained using the method of the present invention, in accordance with a preferred embodiment. The transmitting and receiving antennas are oriented transversely to each other and are spaced apart at varying distances for each induced current decay. The data shown in the graphs of FIGS. 9-16 were acquired with the antennas moving at 3-4 feet per minute along a conductor (2" pipe) wall.
Figure 10:
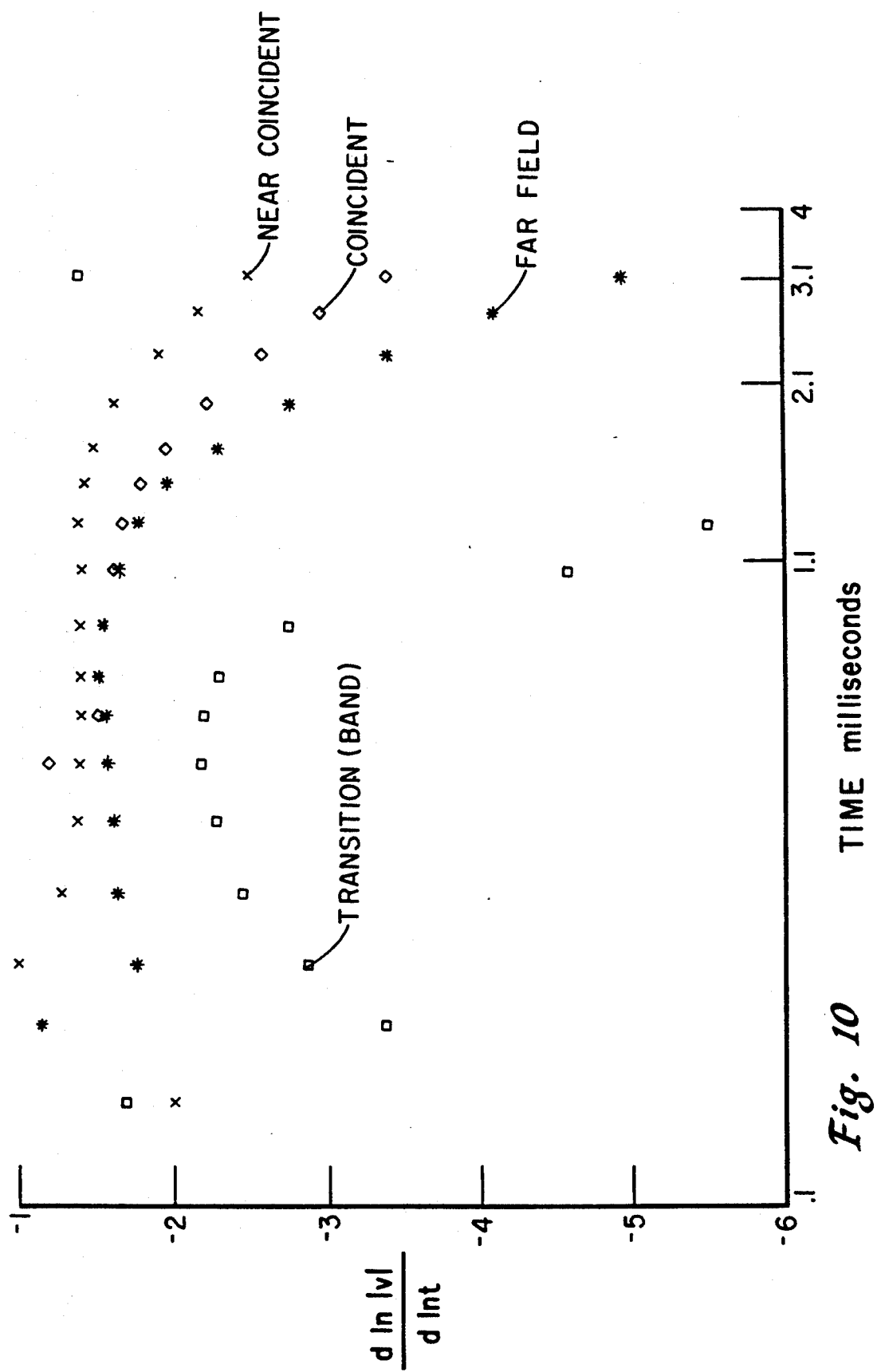
FIG. 10 is a graph showing the logarithmic derivatives of the induced current decays of FIG. 9.
Figure 13:
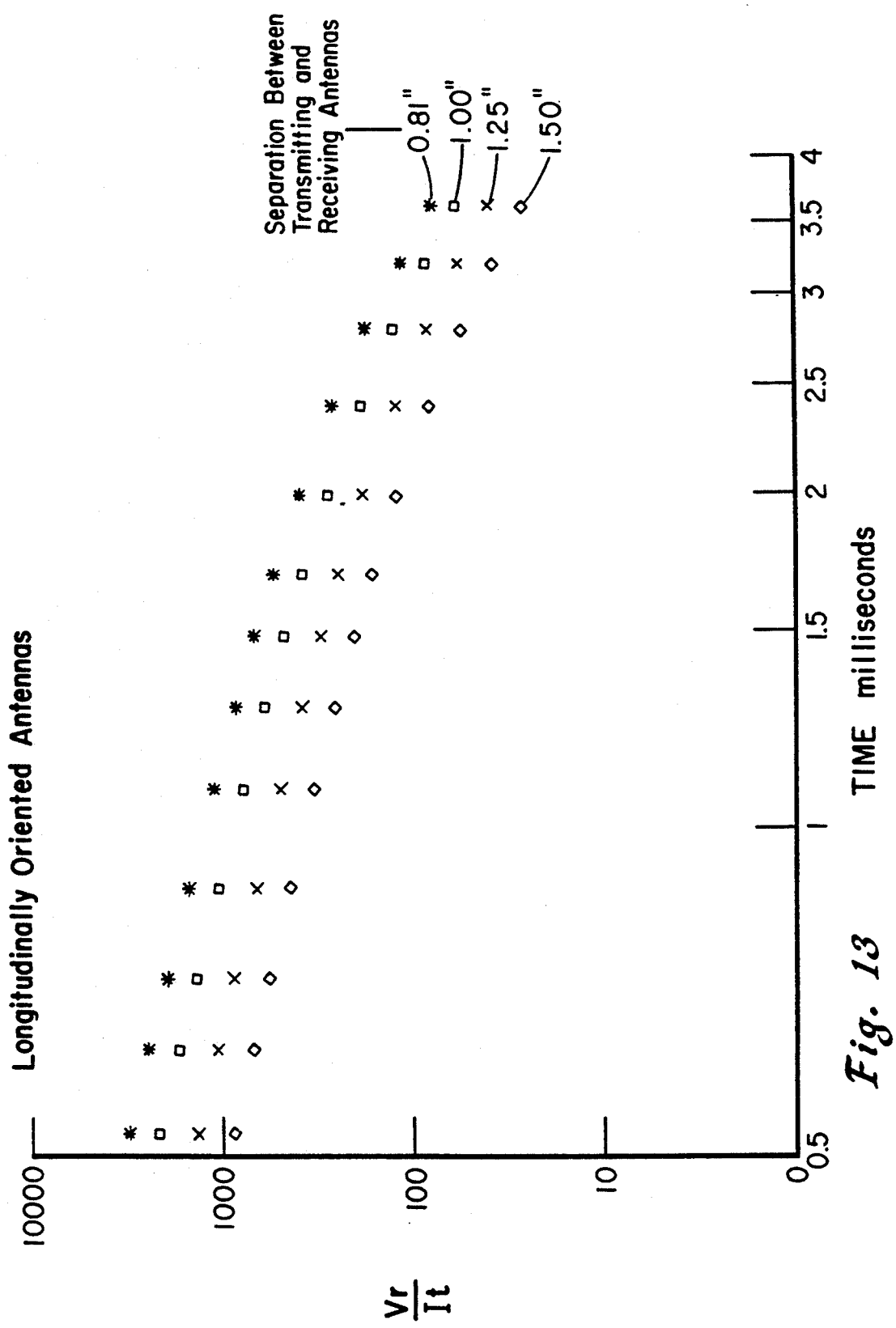
FIG. 13 is a graph showing a decay of induced current in a pipe wall, utilizing longitudinally oriented antennas.

The method of interpreting the received signals depends on the signature of the received signals which in turn depends on the orientation of the respective receiving antenna relative to the transmitting antenna. Referring to FIGS. 4 and 5, there are a coincident receiving antenna 31A, lateral receiving antennas 31B and longitudinal receiving antennas 31C. In FIG. 9, various received signals are shown for a coincident and various transverse receiving antennas. In FIG. 9 (and in FIG. 13) the voltages produced by the receiving antennas have been normalized by removing the effects of variations in coil current. For a coincident receiving antenna and for a near coincident receiving antenna (that is a lateral or transverse receiving antenna 31B that is placed close to the transmitting antenna), the received signals are similar to each other, with the near coincident signal being smaller in magnitude than the coincident signal. Both signals are positive and exhibit a break point in the 1.1-2.1 millisecond time range. The break point for each received signal indicates the time when the induced current reaches the far surface of the wall. As shown in FIG. 10, which shows the logarithmic derivative of the signals in FIG. 9, the break points are indicated by a change in the derivative from a relatively constant value to a suddenly decreasing (i.e. higher negative number) value. The received signal from a transition receiving antenna (that is a lateral receiving antenna that is spaced further from the transmitting antenna than the near coincident antenna) begins with a negative voltage and then crosses zero between 1.1-2.1 milliseconds. After the zero crossover, the signal peaks and then decays to zero. The received signal from a far field receiving antenna (that is a lateral receiving antenna that is spaced further from the transmitting antenna than either the near coincident or the transition antennas) is similar to the coincident and near coincident signals, but is of opposite polarity.

Figure 14:
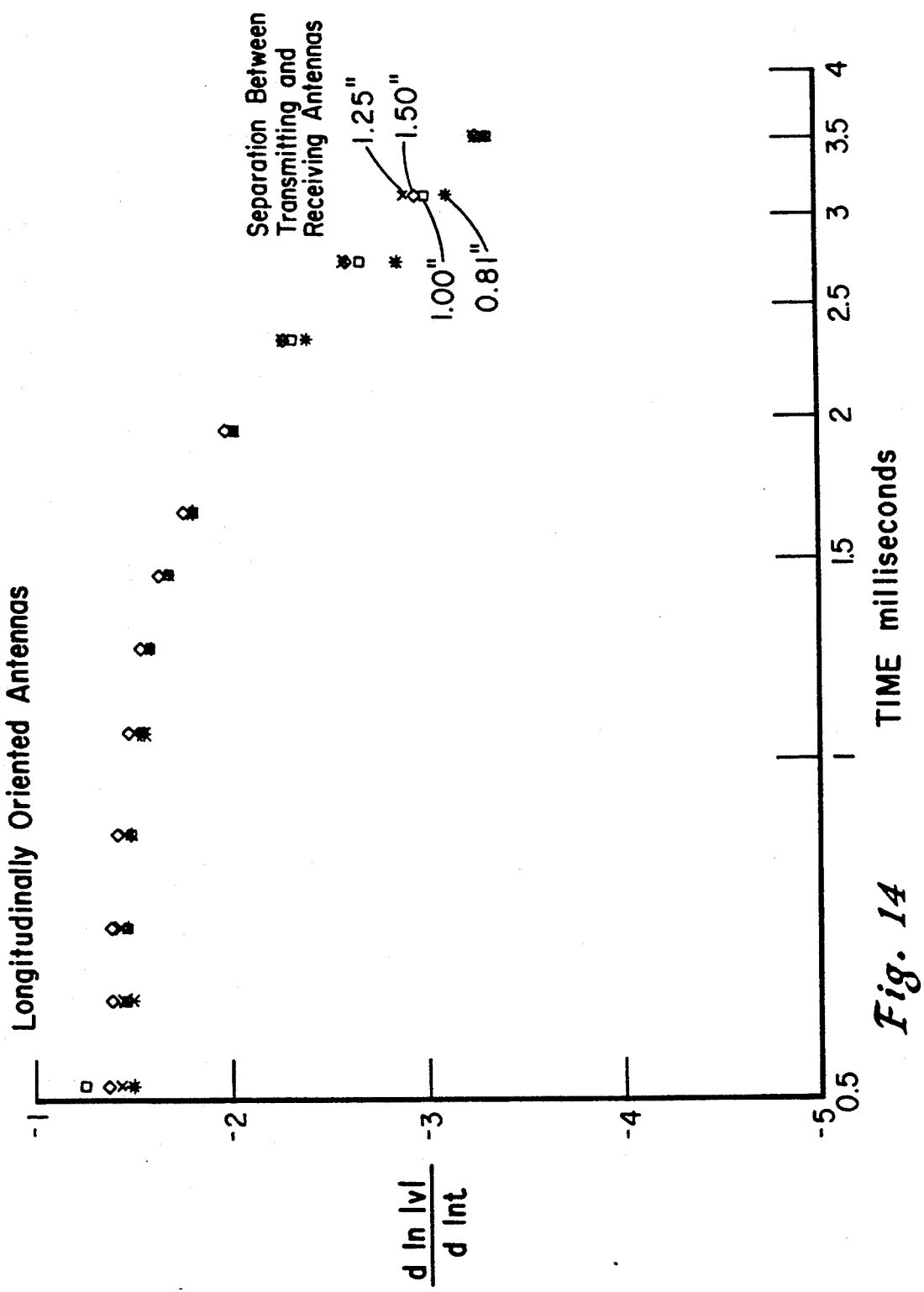
FIG. 14 is a graph showing the logarithmic derivatives of the decays of FIG. 13.

Longitudinally oriented receiving antennas produce received signals that exhibit behavior similar to the coincident and near coincident received signals discussed above (see FIGS. 13 and 14). The received signals decay from a positive maximum voltage that occurs at the beginning. The break point, where the induced currents reach the far surface of the wall, occurs between one and two milliseconds, as shown in FIG. 14. Unlike with lateral receiving antennas, with longitudinal receiving antennas on small pipes the shape of the received signal is independent of the spacing between the transmitting and receiving antennas. Spacing does, however, affect the magnitude of the received signal; the larger the spacing, the lower the magnitude.

The acquired data representing the induced current decay and diffusion in the wall is processed to extract information on the thickness of the wall and/or the presence of any anomalies in the wall. The data is normalized by taking the absolute value and then the logarithmic derivative, as shown in FIG. 10.

The wall thickness (either in quantitative or in qualitative terms) at a particular location is then obtained either by applying an empirically derived relationship or by comparing the derivatives with reference derivatives. The empirical relationship is as follows:

$$th = (d(\ln|V|)/d(\ln t) + 2.17 \ln t - b)/c$$

where th is the wall thickness, V is the voltage as measured by the respective receiving antenna, t is time. The relationship is derived from a linear interpolation algorithm and as such b and c are interpolation constants. The relationship is applicable at intermediate to late times of a received signal, after the occurrence of a break point. The factors b and c are empirically derived and are dependent on wall diameter (in the case of pipes), thickness, metallurgy and temperature. Alternatively, the data can be compared to reference derivatives obtained from walls of known thickness, metallurgy and geometry and obtained with similar antenna geometries. Interpolation may be necessary to determine wall thickness. In the case of received signals obtained with transition receiving antennas, as shown in FIG. 9, the maximum value following the zero crossover and the time of occurrence of that maximum are determined. These two values, the maximum and the time of occurrence are then compared to maximums and times of occurrence of reference transition signals.

Figure 11:
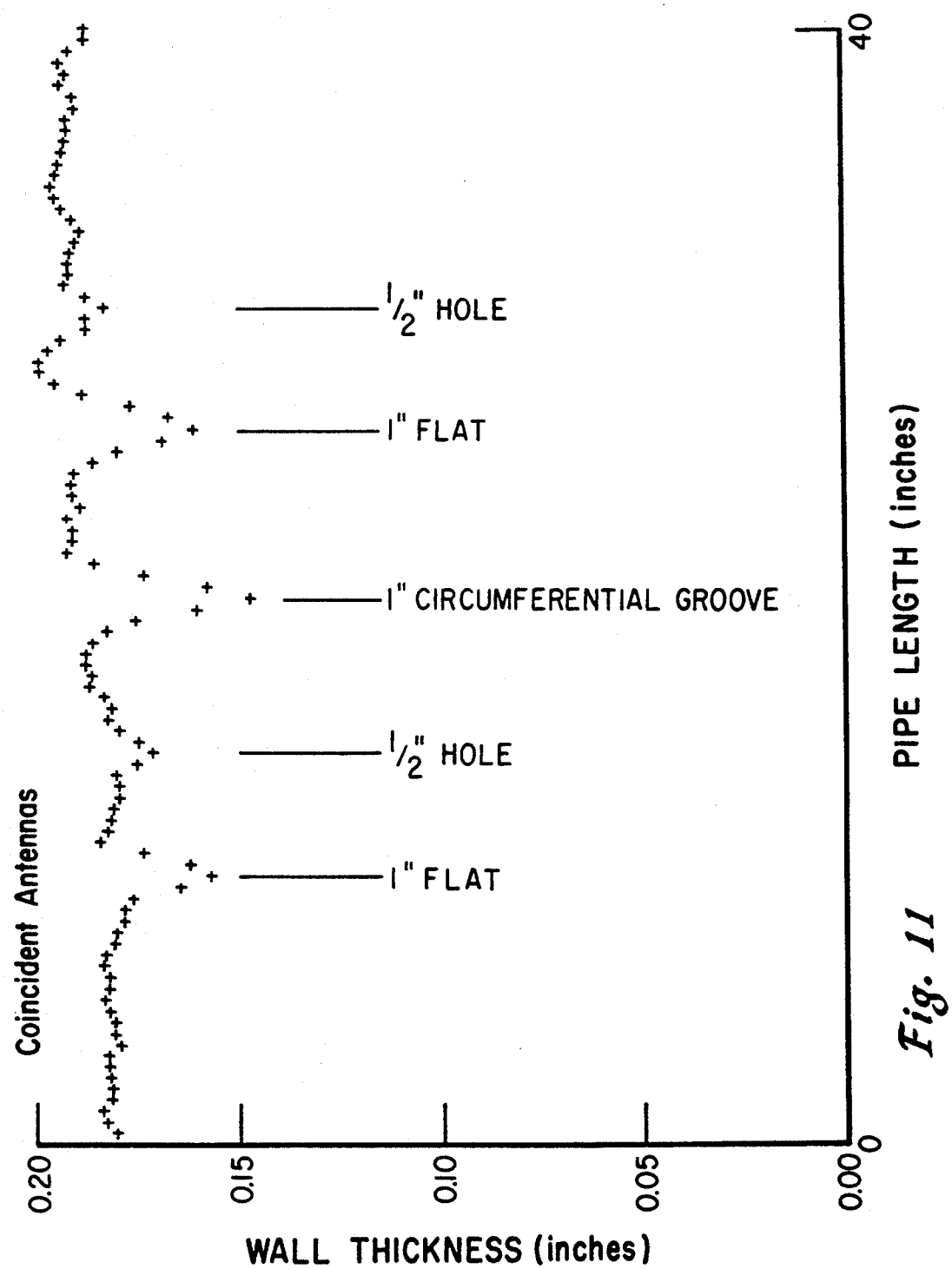
FIG. 11 is a graph showing a survey along a length of pipe, performed with the method of the present invention and using coincident transmitting and receiving antennas.

The wall thickness measurements may then be plotted with reference to their location on the wall. For example, in FIG. 11, there is shown a wall thickness plot along the length of one section of a pipe. The data was obtained using coincident transmitting and receiving antennas moving at 4 feet per minute. Five different anomalies in the wall thickness are shown in FIG. 11. The anomalies were machined on the exterior surface of the wall. The sensors moved along the interior surface of the wall. From left to right, there are a 1 inch diameter flat having an actual wall thickness of 0.137 inches, a ⅛ inch diameter hole having an actual wall thickness of 0.145 inches, a 1 inch wide circumferential groove having an actual wall thickness of 0.153 inches, a 1 inch diameter flat having an actual wall thickness of 0.135 inches, and a ⅛ inch diameter hole having an actual wall thickness of 0.141 inches. The system of the present invention located all of the anomalies and provided reasonable quantative measurements of the wall thickness at the anomalies.

Figure 12:
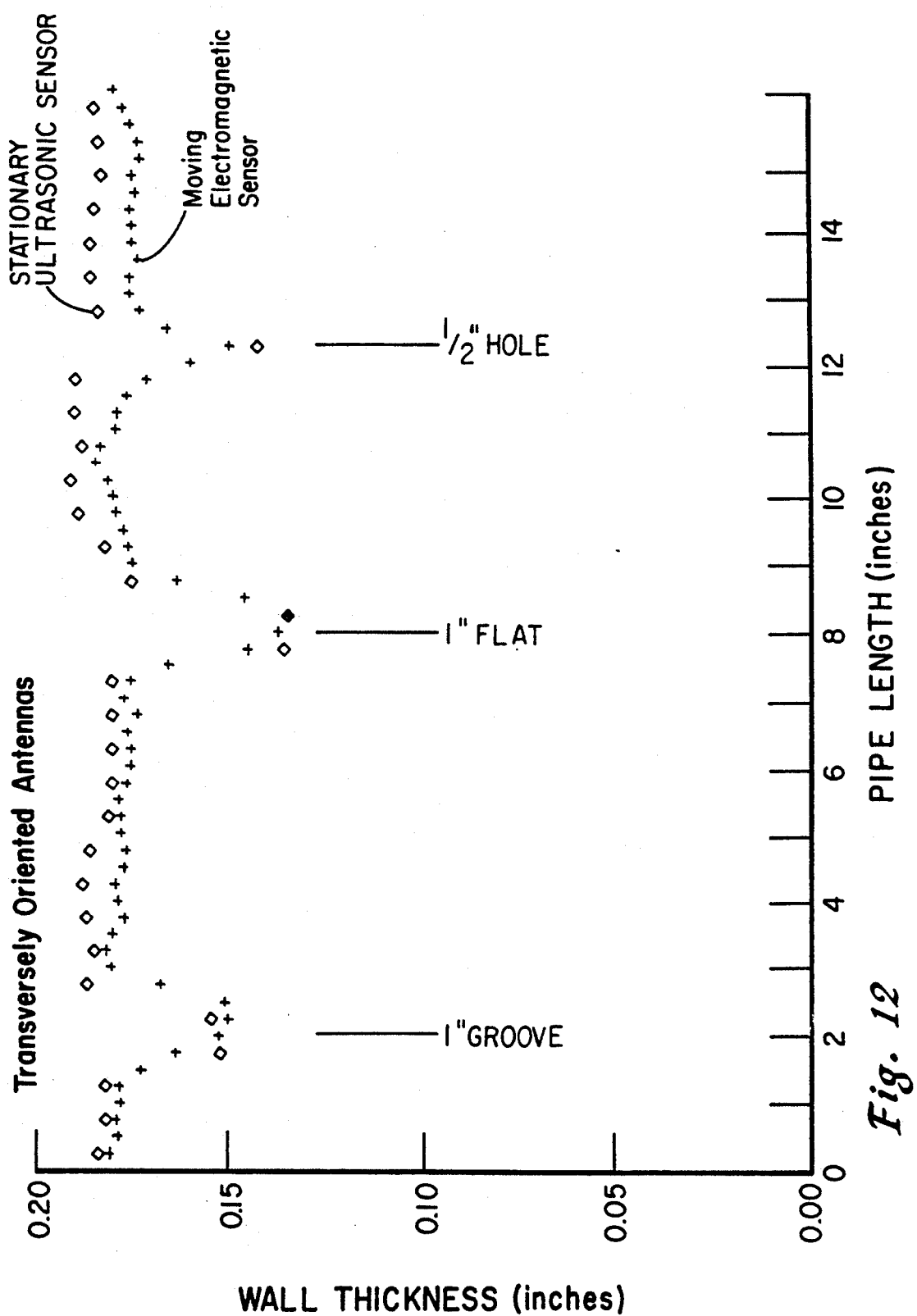
FIG. 12 is a graph showing a survey along a length of pipe, performed using the method of the present invention and using transversely oriented antennas.
Figure 15:
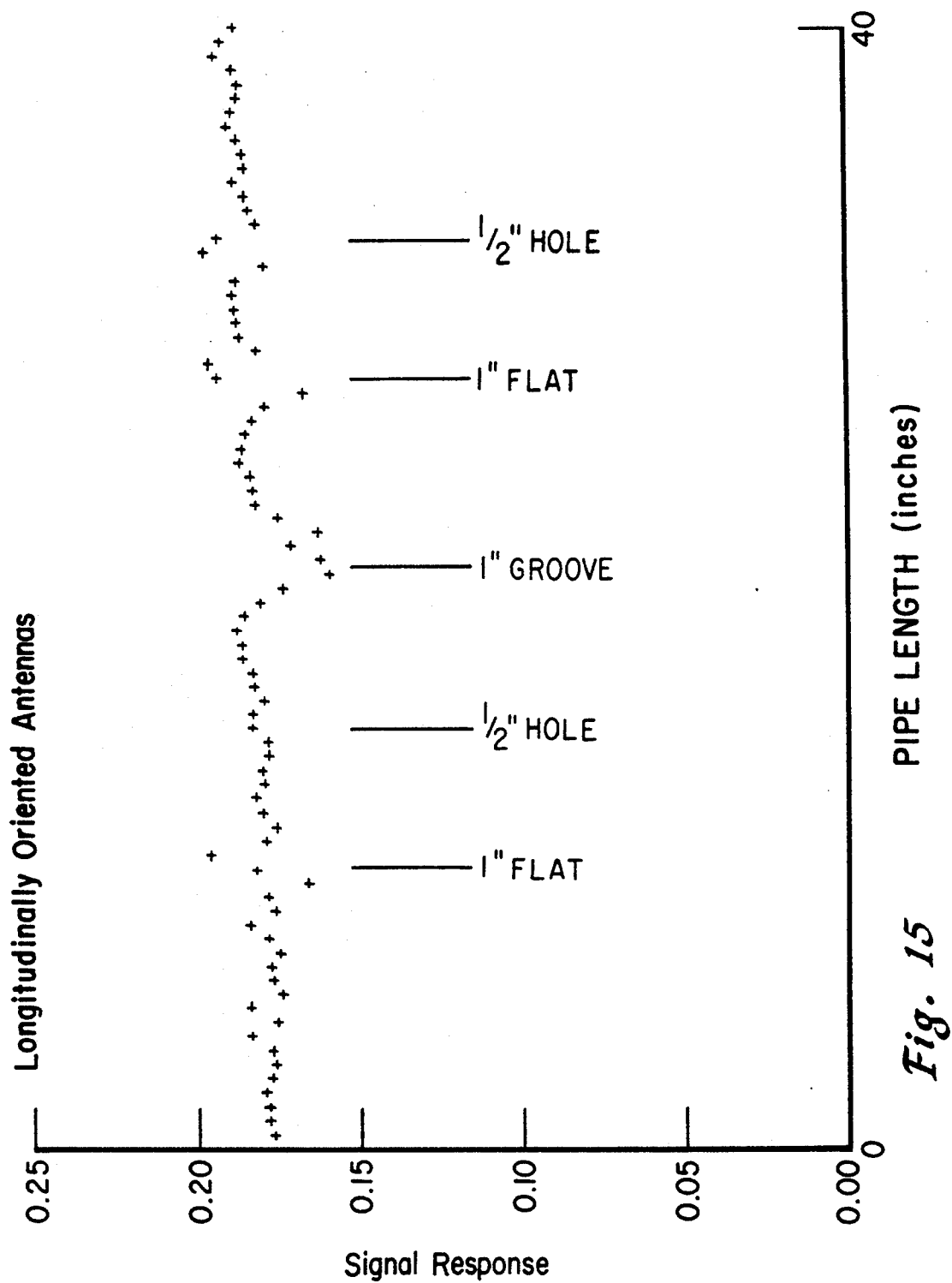
FIGS. 15 and 16 are graphs showing surveys along a length of pipe using longitudinally oriented antennas. The separation between the transmitting and receiving antennas is smaller in the graph shown in FIG. 15 than the separation of the graph shown in FIG. 16.
Figure 16:
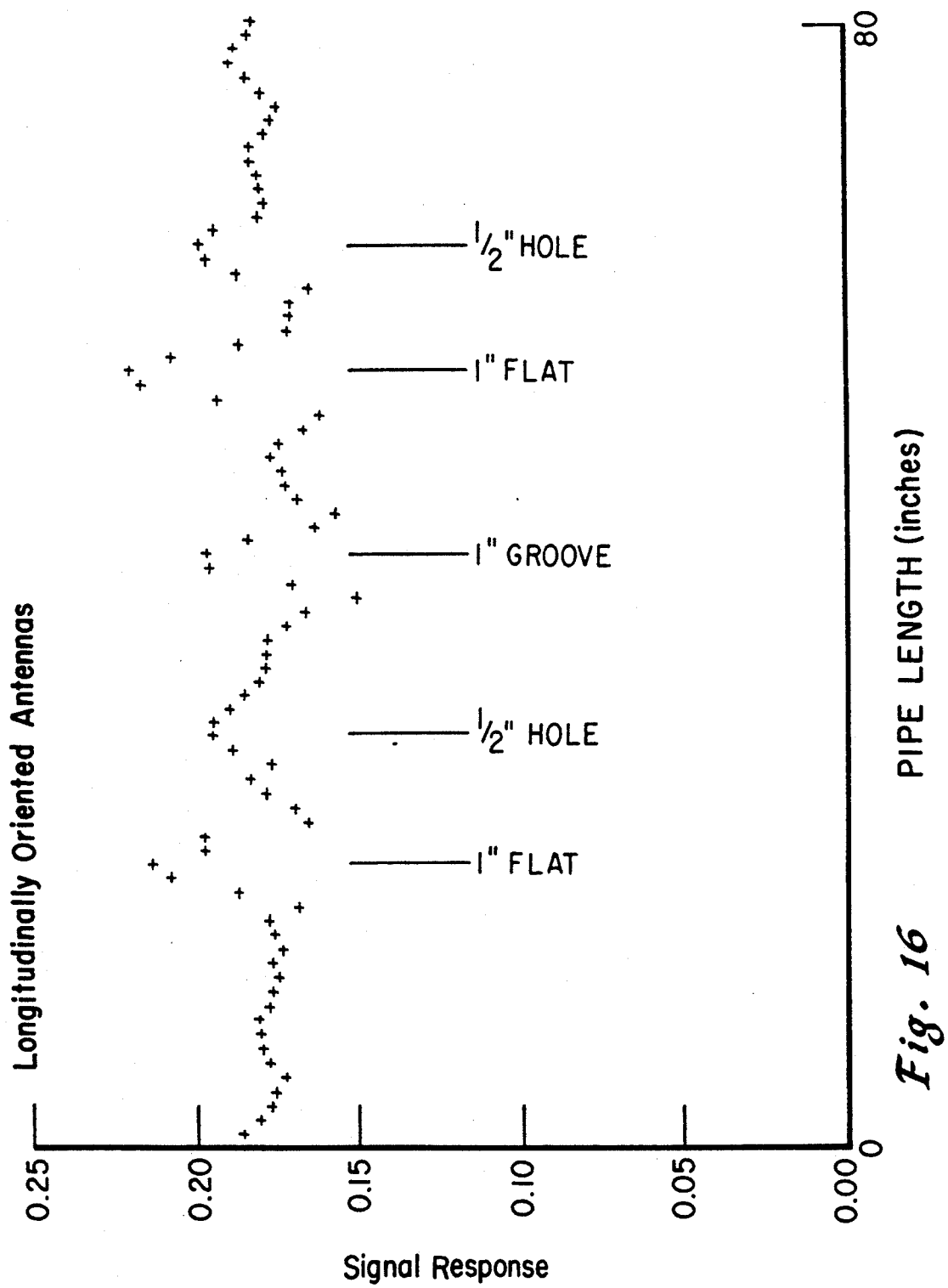

In FIG. 12, there is shown a wall thickness plot along the length of a pipe, obtained with lateral receiving antennas spaced 0.75 inches from the transmitting antenna. The first anomaly is a 1 inch wide circumferential groove, the second anomaly is a 1 inch diameter flat and the third anomaly is a ⅛ inch diameter hole. There is also shown for comparative purposes a stationary ultrasonic survey along the same length of pipe. In FIGS. 15 and 16, there are shown wall thickness plots obtained with longitudinal receiving antennas. In FIG. 15, the longitudinal receiving antenna is spaced 0.81 inches from the transmitting antenna. In FIG. 16, the longitudinal receiving antenna is spaced 2 inches from the transmitting antenna. Better location of some of the anomalies, specifically, the ⅛ inch diameter holes, is achieved with the large antenna spacing.

The use of plural receiving antennas around the transmitting antenna gives much more information about the object under inspection than does a single receiving antenna. I have found that coincident and receiving antennas provide a better signal-to-noise ratio than non-coincidental antennas However noncoincidental antennas, such as the lateral and longitudinal antennas described above, provide better spatial resolution.

Figure 8:
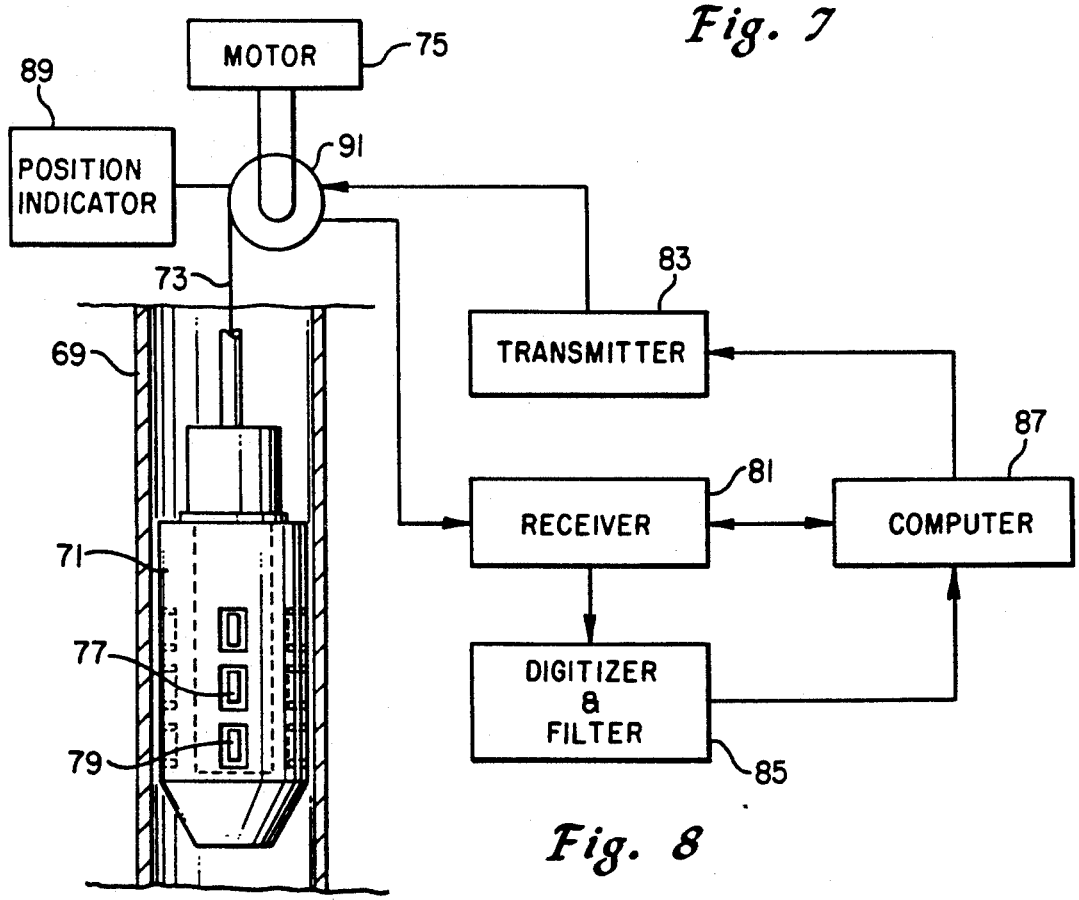
FIG. 8 is a schematic diagram of the downhole electronics.

In FIG. 8, there is shown the apparatus of the present invention, as set up to inspect a length of heat exchanger piping 69. The apparatus includes a probe 71 that is moved through the piping 69 by a cable 73 and motor arrangement 75. The probe 71 has transmitting antennas 77 spaced 90 degrees apart around the outer circumference of the probe. Receiving antennas 79 are spaced longitudinally from each transmitting antenna. A receiver 81 and transmitter 83 are provided, as are a digitizer and filter 85 and a computer 87. A position indicator 89 is coupled to the drum 91 so as to allow a correlation between the data obtained and the position along the piping.

The operation of the apparatus in FIG. 8 is the same as for the apparatus in FIG. 1. Data is obtained and interpreted in the same way. The motor and drum arrangement move the probe through the interior of the heat exchanger piping.

Although the receiving sensors have been described as antennas or coils, the receiving sensors could instead include magnetic flux sensors such as Hall effect devices.

Although the moving means for moving the transmitting antennas and the receiving antennas along the wall which is to be inspected has been described as a motor, drum and cable arrangement, other moving means may be used. Also, the transmitting and receiving antennas need not be located within a pipe or casing; they may be located on the exterior if circumstances permit such placement.

The received signals described herein were obtained by moving sensors longitudinally along a length of pipe. The curvature of the pipe wall produces differences between the transverse and longitudinal receiving antennas. For sensors moving along a flat wall, or a wall with very little curvature, the signatures for the transverse and longitudinal receiving antennas would be similar.

The foregoing disclosure and the showings made in the drawings are merely illustrative of the principles of this invention and are not to be interpreted in a limiting sense.

I claim:

1. A method of inspecting a conductive object, comprising the steps of:
    (a) providing transmitting antenna means and transmitter means connected with said transmitting antennas means;
    b) providing receiving antenna means and receiver means connected with said receiving antenna means;
    c) locating said transmitting antenna means and said receiving antenna means close to said object so as to produce a received signal with a high signal-to-noise ratio;
    d) moving said transmitting antenna means and said receiving antenna means along said object;
    e) while moving said transmitting antenna means and said receiving antenna means along said object providing an abruptly changing current to said transmitting antenna means from said transmitter means so as to induce current into said object and then detecting the induced current in said object with said receiving antenna means to produce said received signal;
    f) determining the thickness of said object from said received signal by determining with respect to time the derivative of said received signal, and comparing the derivative of said received signal to a derivative of a reference signal, said reference signal being obtained from a reference object of known thickness;
    g) repeating step (e) while moving said transmitting antenna means and said receiving antenna means along said object, and repeating step f) with regard to said produced received signals.

2. The method of claim 1 wherein detecting said induced current in said object with said receiving antenna means comprises the step of detecting said portion of said induced current that diffuses from said transmitting antenna means in a direction that is perpendicular to the direction of motion of said transmitting antenna means.

3. The method of claim 1 wherein detecting said induced current in said object with said receiving antenna means comprises the step of detecting said portion of said induced current that diffuses from said transmitting antenna means in a direction that is parallel to the direction of motion of said transmitting antenna means.

4. The method of claim 1 further comprising the step of providing said receiving antenna means coincidentally to said transmitting antenna means such that said receiving antenna means detects said induced current as it diffuses away from said transmitting antenna means.

5. A method of inspecting a conductive object, comprising the steps of:
    a) providing transmitting antenna means and transmitter means connected with said transmitting antennas means;
    b) providing plural receiving antenna means and receiver means connected with said plural receiving antenna means, said plural receiving antenna means being provided as follows:

i) providing a first receiving antenna so as to detect that portion of said induced current that diffuses from said transmitting antenna means in a direction that is perpendicular to the direction of motion of said transmitting antenna means;

ii) providing a second receiving antenna means so as to detect that portion of said induced current that diffuses from said transmitting antenna means in a direction that is parallel to the direction of motion of said transmitting antenna means;

iii) providing a third receiving antenna means coincidentally to said transmitting antenna means such that said third receiving antenna means detects said induced current as it diffuses away from said transmitting antenna means in all directions;

c) locating said transmitting antenna means and said receiving antenna means close to said object so as to produce a received signal with a high signal-to-noise ratio;

d) moving said transmitting antenna means and said receiving antenna means along said object;

e) while moving said transmitting antenna means and with said receiving antenna means along said object providing an abruptly changing current to said transmitting antenna means from said transmitter means so as to induce current into said object and then detecting the induced current in said object with said receiving antenna means to produce said received signal;

f) determining the thickness of said object from said received signal by determining with respect to time the derivative of said received signal, and comparing the derivative of said received signal to a derivative of a reference signal, said reference signal being obtained from a reference object of known thickness;

g) repeating step e) while moving said transmitting antenna means and said receiving antenna means along said object, and repeating step f) with regard to said produced received signals.

6. The method of claim 5 wherein said induced current diffuses in said wall at a diffusion speed, said transmitting antenna means and said receiving antenna means are moved along said wall at a speed that is less than said diffusion speed.

7. A method of inspecting a conductive object, comprising the steps of:

a) providing transmitting antenna means and transmitter means connected with said transmitting antennas means;

b) providing receiving antenna means and receiver means connected with said receiving antenna means;

c) locating said transmitting antenna means and said receiving antenna means in proximity to said object;

d) moving said transmitting antenna means and said receiving antenna means along said object;

e) while moving said transmitting antenna means and said receiving antenna means along said object providing an abruptly changing current to said transmitting antenna means from said transmitter means so as to induce current into said object and then detecting the induced current in said object with said receiving antenna means to produce a received signal;

f) determining the object thickness from said received signal with:

$$th = (d(\ln|V|)/d(\ln t) + 2.17 \ln t - b)/c$$

where th is the wall thickness, V is the voltage as measured by the respective receiving antenna, t is time, and b and c are empirically derived calibration constants.

8. A method of inspecting a conductive object, comprising the steps of:

a) providing transmitting antenna means and transmitter means connected with said transmitting antennas means;

b) providing receiving antenna means and receiver means connected with said receiving antenna means;

c) locating said transmitting antenna means and said receiving antenna means close to said object so as to produce a received signal with a high signal-to-noise ratio, said transmitting antenna means and said receiving antenna means being maintained in a fixed relation to each other;

d) with said transmitting antenna means and said receiving antenna means located at a first position, providing an abruptly changing current to said transmitting antenna means from said transmitter means so as to induce current into said object and then detecting the induced current in said object with said receiving antenna means;

e) continuing to detect the induced current in said object with said receiving antenna means as said transmitting antenna means and said receiving antenna means are moved to a second position along said object, and producing with said receiving antenna means said received signal;

f) determining the thickness of said object from said received signal by determining from said received signal the derivative with respect to time of the decay of said induced current, said derivative having intermediate and late time portions, and comparing said received signal derivative with a derivative of a reference signal, said reference signal being obtained from an object with known thickness;

g) said transmitting antenna means and said receiving antenna means being located and maintained in close proximity to said object during the production of said received signal so that said received signal has a high signal-to-noise ratio, wherein said object thickness can be determined with a single received signal.

9. An apparatus for inspecting a conductive object, comprising:

a) a sensing portion adapted to be located in proximity to said object, said sensing portion comprising transmitting antenna means and plural receiving antenna means, said plural receiving antenna means being provided as follows:

i) a first receiving antenna means is located laterally of said transmitting antenna means such that a first imaginary line extending from said transmitting antenna means to said receiving antenna means is perpendicular to the direction of motion of said sensing portion;

ii) a second receiving antenna means is located relative to said transmitting antenna means such that a second imaginary line extending from said transmitting antenna means to said second receiving antenna means is parallel to the direction of motion of said sensing portion;

iii) a third receiving antenna means is coincident to said transmitting antenna means;

b) transmitter means connected with said transmitting antenna means, said transmitter means producing an abruptly changing current in said transmitting antenna means, and receiver means connected with said plural receiving antenna means;

c) controller means for controlling the operation of said transmitter means and said receiver means such that said transmitter means is operated intermittently to produce said abruptly changing current and such that said receiver means commences operations during each production of said abruptly changing current so as to detect induced currents in said object after each operation of said transmitter means;

d) means for automatically moving said sensing portion along said object during the operation of said transmitter means and said receiver means.

10. The apparatus of claim 9 wherein said moving means comprises a motor and drum, said sensing portion being connected to said drum by a cable, wherein said sensing portion is moved along said wall by rotating said drum.

* * * * *